United States Patent [19]
Hackler et al.

[11] Patent Number: 5,034,393
[45] Date of Patent: Jul. 23, 1991

[54] FUNGICIDAL USE OF PYRIDOPYRIMIDINE, PTERIDINE, PYRIMIDOPYRIMIDINE, PYRIMIDOPYRIDAZINE, AND PYRIMIDO-1,2,4-TRIAZINE DERIVATIVES

[75] Inventors: Ronald E. Hackler, Indianapolis; Glen P. Jourdan, Morristown, both of Ind.

[73] Assignee: DowElanco, Indianapolis, Ind.

[21] Appl. No.: 385,840

[22] Filed: Jul. 27, 1989

[51] Int. Cl.$^5$ ............................................. A01N 43/90
[52] U.S. Cl. ..................... 514/258; 514/249; 514/248; 514/63; 514/278; 544/257; 544/258; 544/256; 544/238; 544/279
[58] Field of Search ............ 514/249, 258, 248, 63, 514/278; 546/345; 544/257, 258, 256, 238, 279

[56] References Cited
U.S. PATENT DOCUMENTS
4,101,554  7/1989  Tobin ........................ 260/290 HC FOREIGN PATENT DOCUMENTS
920267  5/1959  United Kingdom ............... 544/257

OTHER PUBLICATIONS

Sankyo Co., Chemical Abstracts, vol. 94:1068f and attached 10th collected index, p. 46420CS.
E. C. Taylor et al., 82 *J.A.C.S.* 5711-5718 (1960).
S. Nishikawa et al., 50 *Agric. Biol. Chem.*, 2243-2249 (1986).
S. Nishikawa et al., 50 *Agric. Biol. Chem.*, 495-497 (1986).
H. Iwamura et al., 28 *J. Med. Chem.*, 577-583 (1985).
Derwent Abst. 86-001168/01 (1986) abstracting EP 165,572A.
Derwent Abst. 80-70448C/40 (1980) abstracting JP 55108806.

Primary Examiner—Mukund J. Shah
Assistant Examiner—M. V. Grumbling
Attorney, Agent, or Firm—Donald R. Stuart

[57] ABSTRACT

Fungicidal compositions contain as active ingredient a 4-substituted-pyrido[3,2-d]pyrimidine, -pyrido[4,3-d]pyrimidine, -pyrido[3,4-d]pyrimidine, pyrido[2,3-d]pyrimidine, -pteridine, -pyrimido[4,5-d]pyrimidine, -pyrimido[4,5-c]pyridazine, -pyrimido[5,4-d]pyrimidine, -pyrimido[5,4-c]pyridazine, pyrimido[4,5-d]pyridazine, or -pyrimido[5,4-e]-1,2,4-triazine, for example 4-[2-(4-chlorophenyl)ethoxy]pyrido[2,3-d]pyrimidine.

40 Claims, No Drawings

FUNGICIDAL USE OF PYRIDOPYRIMIDINE, PTERIDINE, PYRIMIDOPYRIMIDINE, PYRIMIDOPYRIDAZINE, AND PYRIMIDO-1,2,4-TRIAZINE DERIVATIVES

FIELD OF THE INVENTION

This invention provides new compounds that have excellent plant fungicide activity. Some of the compounds have also demonstrated insecticidal and miticidal activity. The invention also provides compositions and combination products that contain a compound of the invention as active ingredient, as well as providing fungicidal, miticidal, and insecticidal methods.

There is an acute need for new fungicides, insecticides, and miticides, because target pathogens are rapidly developing resistance to currently used pesticides. Widespread failure of N-substituted azole fungicides to control barley mildew was observed in 1983, and has been attributed to the development of resistance. At least 50 species of fungi have developed resistance to the benzimidazole fungicides. The field performance of DMI (demethylation inhibitor) fungicides, which are now widely relied on to protect cereal crops from powdery mildew, has declined since they were introduced in the 1970's. Even recently introduced fungicides, like the acylalanines, which initially exhibited excellent control of potato late blight and grape downy mildew in the field, have become less effective because of widespread resistance. Similarly, mites and insects are developing resistance to the miticides and insecticides in current use. Resistance to insecticides in arthropods is widespread, with at least 400 species resistant to one or more insecticides. The development of resistance to some of the older insecticides, such as DDT, the carbamates, and the organophosphates, is well known. But resistance has even developed to some of the newer pyrethroid insecticides and miticides. Therefore a need exists for new fungicides, insecticides, and miticides.

SUMMARY OF THE INVENTION

This invention provides compounds of the formula (1):

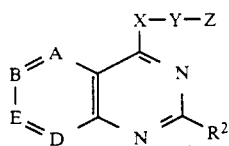

(1)

wherein
one or two of A, B, E, or D are N, and the others are $CR^1$ or A, E, and D are N and B is $CR^1$; where $R^1$ and $R^2$ are independently H, halo, $(C_1-C_4)$ alkyl, $(C_3-C_4)$ branched alkyl, $(C_1-C_4)$ alkoxy, halo $(C_1-C_4)$ alkyl, phenyl, or substituted phenyl;

X is O, S, SO, $SO_2$, $NR^3$, or $CR^4R^5$, where $R^3$ is H, $(C_1-C_4)$ alkyl, or $(C_1-C_4)$ acyl, and $R^4$ and $R^5$ are independently H, $(C_1-C_4)$ acyl, $(C_1-C_4)$ alkyl, $(C_2-C_4)$ alkenyl or -alkynyl, CN, or OH, or $R^4$ and $R^5$ combine to form a carbocyclic ring containing four to six carbon atoms;

Y is a bond or an alkylene chain one to six carbon atoms long, optionally including a carbocyclic ring, and optionally including a hetero atom selected from O, $NR^3$, S, SO, $SO_2$, or $SiR^{20}R^{21}$, where $R^3$ is as defined above and $R^{20}$ and $R^{21}$ are independently $(C_1-C_4)$ alkyl, $(C_3-C_4)$ branched alkyl, phenyl, or substituted phenyl, and optionally substituted with $(C_1-C_4)$ alkyl, $(C_2-C_4)$ alkenyl or -alkynyl, branched $(C_3-C_7)$ alkyl, $C_3-C_7$ cycloalkyl or -cycloalkenyl, halo, hydroxy, or acetyl, and Z is
(a) a $C_1-C_{12}$ saturated or unsaturated hydrocarbon chain, straight chain or branched optionally including a hetero atom selected from O, S, SO, $SO_2$, or $SiR^{20}R^{21}$, where $R^{20}$ and $R^{21}$ are as defined above and optionally substituted with halo, halo $(C_1-C_4)$ alkoxy, hydroxy, $(C_3-C_8)$ cycloalkyl or cycloalkenyl, or $(C_1-C_4)$ acyl;

(b) $(C_3-C_8)$ cycloalkyl or cycloalkenyl, optionally substituted with $(C_1-C_4)$ alkyl, $(C_1-C_4)$ alkoxy, halo $(C_1-C_4)$ alkyl, halo $(C_1-C_4)$ alkoxy, halo, hydroxy, or $(C_1-C_4)$ acyl;

(c) a phenyl group of the formula (2)

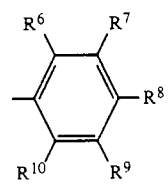

(2)

where
$R^6$ to $R^{10}$ are independently H, halo, I, $(C_1-C_{10})$ alkyl, $(C_3-C_8)$ alkenyl or -alkynyl, branched $(C_3-C_6)$ alkyl, -alkenyl, or -alkynyl, $(C_3-C_8)$ cycloalkyl or -cycloalkenyl, halo $(C_1-C_7)$ alkyl, $(C_1-C_7)$ alkoxy, $(C_1-C_7)$ alkylthio, halo $(C_1-C_7)$ alkoxy, phenoxy, substituted phenoxy, phenylthio, substituted phenylthio, phenyl, substituted phenyl, $NO_2$, acetoxy, OH, CN, $SiR^{11}R^{12}R^{13}$, $OSiR^{11}R^{12}R^{13}$, $NR^{14}R^{15}$, $S(O)R^{16}$, or $SO_2R^{17}$ where $R^{11}$, $R^{12}$, and $R^{13}$ are independently $(C_1-C_4)$ alkyl, $(C_3-C_4)$ branched alkyl, phenyl, or substituted phenyl, $R^{14}$ and $R^{15}$ are independently H, $(C_1-C_4)$ alkyl, or $(C_3-C_4)$ acyl, and $R^{16}$ and $R^{17}$ are $(C_1-C_{10})$ alkyl, phenyl, or substituted phenyl;

(d) a furyl group of formula (3)

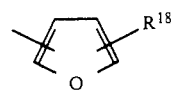

(3)

where $R^{18}$ is H, halo, halomethyl, CN, $NO_2$, $(C_1-C_4)$ alkyl, $(C_3-C_4)$ branched alkyl, phenyl, or $(C_1-C_4)$ alkoxy;

(e) a thienyl group of the formula (4)

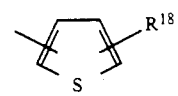

(4)

where $R^{18}$ is as defined in paragraph (d);

(f) a group of formula (5) or (6)

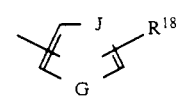

(5)

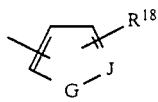

(6)

where $R^{18}$ is as defined in paragraph (d), J is N or CH, and G is O, $NR^{19}$, or S, provided that if J is not N then G is $NR^{19}$, where $R^{19}$ is H, $(C_1-C_4)$ alkyl, $(C_1-C_4)$ acyl, phenylsulfonyl, or substituted phenylsulfonyl;

(g) a group selected from
optionally substituted naphthyl, dihydronaphthyl, tetrahydronaphthyl, and decahydronaphthyl;
optionally substituted pyridyl;
optionally substituted indolyl;
and 1,3-benzodioxolyl;
or an acid addition salt of a compound of formula (1);
provided that the following compounds are excluded:

1) pyrido[2,3-d]pyrimidines of formula (1) wherein X is $NR^3$ and —Y—Z is benzyl, or X is $NR^3$, Y is an alkylene chain containing an O or S atom adjacent to Z, and Z is either unsubstituted phenyl or a substituted phenyl group other than one substituted with
branched $(C_3-C_6)$ alkyl,
halo $(C_1-C_4)$ alkyl,
halo $(C_1-C_4)$ alkoxy,
phenyl,
substituted phenyl,
phenoxy,
substituted phenoxy,
phenylthio,
substituted phenylthio,
$SiR^{11}R^{12}R^{13}$, or
$OSiR^{11}R^{12}R^{13}$;

2) pyrido[3,4-d]pyrimidines of formula (1) wherein X is $NR^3$, Z is unsubstituted phenyl, and $R^2$ is methyl; and 3) pyrido[3,4-d]pyrimidines of formula (1) wherein X is $NR^3$ and —Y—Z is benzyl or isoamyl.

Proviso (1) excludes compounds that are described as fungicides in Japanese patent application 55108806 of Sankyo. Proviso (2) excludes compounds for which cytokinin activity is reported in *Agri. Biol. Chem.*, 50, 2243-49 (1986). Proviso (3) excludes compounds for which cytokinin activity is reported in *Agri. Biol. Chem.*, 50, 495-97 (1986).

The fungicide combinations of the invention comprise at least 1% by weight of a compound of formula (1), excluding compounds of proviso (1) but including those of provisos (2) and (3), in combination with a second plant fungicide.

The fungicide compositions of the invention comprise a disease inhibiting and phytologically acceptable amount of compound of formula (1), excluding compounds of proviso (1) but including those of provisos (2) and (3), in combination with a phytologically-acceptable carrier. Such compositions may optionally contain additional active ingredients, such as an additional fungicidal, miticidal, or insecticidal ingredient.

The fungicidal method of the invention comprises applying to the locus of a plant pathogen a disease inhibiting and phytologically acceptable amount of a compound of formula (1), excluding compounds of proviso (1) but including those of provisos (2) and (3).

The insecticide and miticide combinations of the invention comprise at least 1% by weight of a compound of formula (1), including compounds of provisos (1) to (3), in combination with a second insecticide or miticide.

The insecticide and miticide compositions of the invention comprise an insect- or mite-inactivating amount of a compound of formula (1), including compounds of provisos (1) to (3), in combination with a carrier. Such compositions may optionally contain additional active ingredients, such as an additional fungicidal, miticidal, or insecticidal ingredient.

The insecticidal or miticidal method of the invention comprises applying to the locus to be protected an insect- or mite-inactivating amount of a compound of formula (1), including compounds of provisos (1) to (3), or of a combination described above.

DETAILED DESCRIPTION OF THE INVENTION

Throughout this document, all temperatures are given in degrees Celsius, and all percentages are weight percentages unless otherwise stated.

The term "halo" refers to a F, Cl, or Br atom.

The term "$(C_1-C_7)$ alkoxy" refers to straight or branched chain alkoxy groups.

The term "$(C_1-C_7)$ alkylthio" refers to straight and branched chain alkylthio groups.

The term "halo $(C_1-C_7)$ alkyl" refers to a $(C_1-C_7)$ alkyl group, straight chain or branched, substituted with one or more halo atoms.

The term "halo $(C_1-C_7)$ alkoxy" refers to a $(C_1-C_7)$ alkoxy group substituted with one or more halo groups.

The term "halo $(C_1-C_4)$ alkylthio" refers to a $(C_1-C_4)$ alkylthio group, straight chain or branched, substituted with one or more halo atoms.

The term "substituted phenyl" refers to phenyl substituted with up to three groups selected from halo, I, $(C_1-C_{10})$ alkyl, branched $(C_3-C_6)$ alkyl, halo $(C_1-C_4)$ alkyl, hydroxy $(C_1-C_4)$ alkyl, $(C_1-C_4)$ alkoxy, halo $(C_1-C_4)$ alkoxy, phenoxy, substituted phenoxy, phenyl, substituted phenyl, $NO_2$, OH, CN, $(C_1-C_4)$ alkanoyloxy, or benzyloxy.

The terms "substituted naphthyl", "substituted pyridyl" and "substituted indolyl" refer to these ring systems substituted with halo, halo $(C_1-C_4)$ alkyl, CN, $NO_2$, $(C_1-C_4)$ alkyl, $(C_3-C_4)$ branched alkyl, phenyl, substituted phenyl, $(C_1-C_4)$ alkoxy, or halo $(C_1-C_4)$ alkoxy.

The term "substituted phenoxy" refers to phenoxy substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, substituted phenoxy, phenyl, substituted phenyl, $NO_2$, OH, CN, $(C_1-C_4)$ alkanoyloxy, or benzyloxy.

The term "carbocyclic ring" refers to a saturated or unsaturated carbocyclic ring containing three to seven carbon atoms.

The terms "substituted phenylthio" and "substituted phenyl sulfonyl" refer to such groups substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, substituted phenoxy, phenyl, substituted phenyl, $NO_2$, OH, CN, $(C_1-C_4)$ alkanoyloxy, or benzyloxy.

The term "unsaturated hydrocarbon chain" refers to a hydrocarbon chain containing one or two sites of unsaturation.

The term "HPLC" refers to a high-performance liquid chromatography.

COMPOUNDS

Compounds of formula (1) wherein A is N and B, E, and D are $CR^1$ are pyrido [3,2-d]pyrimidines.

Compounds of formula (1) wherein B is N and A, E, and D are $CR^1$ are pyrido [4,3-d]pyrimidines.

Compounds of formula (1) wherein E is N and A, B, and D are $CR^1$ are pyrido[3,4-d]pyrimidines.

Compounds of formula (1) wherein D is N and A, B, and E are $CR^1$ are pyrido[2,3-d]pyrimidines.

Compounds of formula (1) wherein A and D are N and B and E are $CR^1$ are pteridines (or pyrazino[2,3-d]pyrimidines.

Compounds of formula (1) wherein B and D are N and A and E are $CR^1$ are pyrimido[4,5-d]pyrimidines.

Compounds of formula (1) wherein E and D are N and A and B are $CR^1$ are pyrimido[4,5-c]pyridazines.

Compounds of formula (1) wherein A and E are N and B and D are $CR^1$ are pyrimido[5,4-d]pyrimidines.

Compounds of formula (1) wherein A and B are N and E and D are $CR^1$ are pyrimido[5,4-c]pyridazines.

Compounds of formula (1) wherein B and E are N and A and D are $CR^1$ are pyrimido[4,5-d]pyridazines.

Compounds of formula (1) wherein A, E, and D are N and B is $CR^1$ are pyrimido[5,4-e]-1,2,4-triazines.

While all of the compounds of the invention are useful fungicides, certain classes are preferred for reasons of greater efficacy or ease of synthesis, viz:

(a) compounds of formula (1) wherein one of A, B, E, and D is N and the rest are $CR^1$.

(b) compounds of class (a) wherein D is N and A, B, and E are $CR^1$, i.e., pyrido[2,3-d]pyrimidine derivatives;

(c) compounds of formula (1) wherein Z is substituted phenyl;

(d) compounds of formula (1) wherein X is O; and (e) compounds of class (d) wherein Y is a chain at least two atoms long.

SYNTHESIS

The compounds of this invention are made using well known chemical procedures. The required starting materials are commercially available, or they are readily synthesized using standard procedures.

Synthesis of Compounds Wherein X is O

The compounds of formula (1) wherein X is O are made by condensing a compound of formula (7):

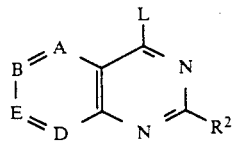

where $R^2$, A, B, E, and D are as previously defined, and L is a leaving group such as F, Cl, Br, I, $NO_2$, 1,2,4-triazol-1-yl, $-O-Si(Me)_3$, arylthio, alkylthio, alkylsulfonyl, arylsulfonyl, alkoxy, or arylsulfinyl with an alcohol or phenol of the formula (8):

where

Y and Z are as previously defined.

For many of the examples, the reaction was carried out in toluene treated with dry HCl, at room temperature or with gentle heating.

Alternatively, and preferably, the reaction may be carried out in the presence of a strong base, such as sodium hydride, in a non-reactive organic solvent, such as DMF, at a temperature in the range of 0 to 25° C.

Synthesis of Compounds Wherein X is $NR^3$

The compounds of formula (1) wherein X is $NR^3$ are prepared by condensing a compound of formula (7) with an amine of the formula (9)

where $R^3$, is H or $((C_1-C_4)$ alkyl, and

Y and Z are as previously defined.

The chloride of formula (7) is allowed to react with an appropriate amine at a wide variety of temperatures (20-180° C.), preferably in the presence of an acid acceptor, such as triethylamine. The reaction may be carried out neat, or in a non-reactive organic solvent. Compounds where $R^3$ is acyl are prepared from amines where $R^3$ is H, which were allowed to react with an acylating agent such as acetyl chloride or acetic anhydride. In cases where the starting material of formula (7) is one wherein $R^1$ or $R^2$ is Cl, a mixture of products is obtained which are separable using liquid chromatography.

Synthesis of Compounds Wherein X is $CH_2$

The compounds of formula (1) wherein X is $CH_2$ can be made using the process described in J. Heterocyclic Chemistry, Vol. 14, p. 1081-1083 (1977) by A. Scoville and F. X. Smith. This process entails preparation of a barbituric acid of the formula (10)

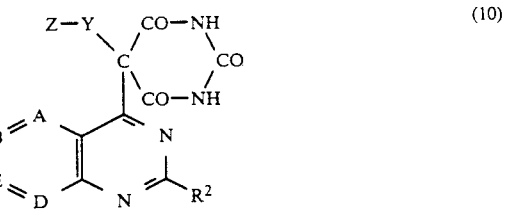

which is then hydrolyzed and decarboxylated by dissolving the intermediate in a solution of sodium hydroxide and water, refluxing, then making the solution slightly acidic with hydrochloric acid and again refluxing.

The acid addition salts of compounds of formula (1) are obtained in the usual way.

Accordingly, the invention also provides a process for preparing a compound of formula (1) which comprises (a) condensing a compound of formula (7)

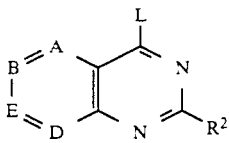

(7)

wherein $R^1$, $R^2$, A, B, E, and D are as previously defined, and L is a leaving group with an alcohol of the formula (8):

$$HO-Y-Z \quad (8)$$

wherein Y and Z are as previously defined to produce a compound of formula (1) wherein X is ; or (b) condensing a compound of formula (7) as defined above with an amine of the formula (9)

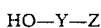

(9)

where $R^{3'}$ is H or $(C_1-C_4)$ alkyl, and Y and Z are as previously defined, to provide a compound of formula (1) where X is $NR^3$; or (c) acylating a compound of formula (1) wherein X is $NR^{3'}$ to provide a compound of formula (1) wherein X is $NR^3$ and $R^3$ is acyl; or (d) hydrolyzing and decarboxylating a compound of formula (10)

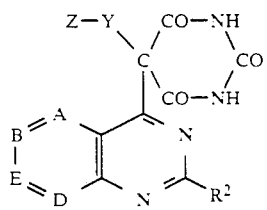

(10)

to produce a compound of formula (1) wherein X is $CH_2$.

Preparation of Pyridopyrimidine, Pyrimidopyrimidine, and Pteridine Starting Materials 4-Hydroxypyridopyrimidine starting materials are commercially available or readily prepared using conventional procedures. For example, useful synthetic procedures are described in R. K. Robins & G. H. Hitchings, *J. Am. Chem. Soc.*, 77, 2256 (1955);

S. Gabriel & J. Colman, *Chem. Ber.*, 35, 2831 (1902); and

C. C. Price & D. Y. Curtin, *J. Am. Chem. Soc.*, 68, 914 (1946).

4-Hydroxypyrimido[4,5-d]pyrimidines can be prepared using the procedure described in E. C. Taylor, et al., *J. Amer. Chem. Soc.*, 82, 6058 (1960).

4-Hydroxypteridines can be prepared using the procedures described in A. Albert, D. J. Brown and G. Cheesman, *J. Chem. Soc.*, 474 (1951).

4-Hydroxypyrimido[4,5-c]pyridazines can be prepared by the procedures described in J. L. Styles and R. W. Morrison, *J. Org. Chem.*, 50, 346 (1985).

4-Hydroxypyrimido[5,4-d]pyrimidines can be prepared by the procedures described in F. A. Gianturro, P. Gramaccioni, and A. Vaciago, *Gazz. Chim. Ital.*, 99, (1969).

4-Hydroxypyrimido[5,4-c]pyridazines can be prepared by the procedures described in R. N. Castle and H. Murakami, *J. Hetero. Chem.*, 5, 523 (1968).

4-Hydroxypyrimido[4,5-d]pyridazines can be prepared by the procedures described in R. N. Castle, *J. Hetero. Chem.*, 5, 845 (1968).

4-Chloro derivatives of formula (7) wherein L is Cl are prepared by chlorodehydroxylation of the corresponding 4-keto compounds using conventional methods, for example by reaction with $POCl_3$.

Intermediates of formula (7) wherein L is 1,2,4-triazol-1-yl, can be prepared, for example, by adding $POCl_3$ dropwise to a mixture of a 4-hydroxypyridopyrimidine (1 equiv.) and 1,2,4-triazole (3 equiv.) in pyridine at a temperature from 20 to 100° C.

EXAMPLES 1-72

The following examples are compounds actually prepared by the above described general procedures. The melting point is given for each compound. In addition, although the data has not been included, each compound was fully characterized by NMR, IR, mass spectra, and combustion analysis. Specific illustrative preparations for the compounds of Examples follow the tabular listing.

| EXAMPLE NUMBER | COMPOUND | M.P. |
|---|---|---|
| 1 | 4-(4-fluorophenoxy)pyrido[2,3-d]pyrimidine | 142-144° C. |
| 2 | 4-[2-[4-(i-propyl)phenyl]ethylamino]pyrido[2,3-d]pyrimidine | 198-200° C. |
| 3 | 4-[2-(4-chlorophenyl)ethoxy]pyrido-[2,3-d]pyrimidine | 126-128° C. |
| 4 | 4-[2-(4-chlorophenyl)ethoxy]pyrido-[3,2-d]pyrimidine | 86° C. |
| 5 | 4-[2-[4-(t-butyl)phenyl]ethylamino]-pyrido[3,2-d]pyrimidine | 77-78° C. |
| 6 | 4-(2-chloro-4-fluorophenoxy)pyrido-[2,3-d]pyrimidine | 181-182° C. |
| 7 | 4-[2-(4-ethoxyphenyl)ethoxy]pyrido-[3,2-d]pyrimidine | 74-75° C. |
| 8 | N-(2-phenylethyl)pyrido[2,3-d]-pyrimidin-4-amine | 252-254° C. |
| 9 | N-[2-(2-naphthalenyl)ethyl]pyrido-[2,3-d]pyrimidin-4-amine | 247-251° C. |
| 10 | 4-[2-(2,4-difluorophenyl)ethoxy]-pyrido[2,3-d]pyrimidine | 84-85° C. |
| 11 | 4-[2-(4-ethoxyphenyl)ethoxy]pyrido-[2,3-d]pyrimidine | 62-64° C. |
| 12 | N-[2-[3-(trifluoromethyl)phenyl]-ethyl]pyrido[2,3-d]pyrimidin-4-amine | 190-193° C. |
| 13 | N-(4-phenylbutyl)pyrido[2,3-d]-pyrimidin-4-amine | 179-181° C. |
| 14 | N-(3-phenylpropyl)pyrido[2,3-d]-pyrimidin-4-amine | 195-198° C. |
| 15 | 4-(2-phenylethoxy)pyrido[2,3-d]-pyrimidine | 101-102° C. |
| 16 | N-[2-(4-chlorophenyl)ethyl]pyrido-[2,3-d]pyrimidin-4-amine | 271-275° C. |
| 17 | 4-[2-(4-methoxy-3-methylphenyl)-ethoxy]pyrido[2,3-d]pyrimidine | 113-114° C. |
| 18 | 4-[3-(4-phenoxyphenyl)propoxy]-pyrido[2,3-d]pyrimidine | oil |
| 19 | N-[(4-chlorophenyl)methyl]pyrido-[2,3-d]pyrimidin-4-amine | 252-255° C. |
| 20 | N-[2-(2,6-difluorophenyl)ethyl]-pyrido[2,3-d]pyrimidin-4-amine | 263-266° C. |
| 21 | 4-[2-[4-(trimethylsilyl)phenyl]-ethoxy]pyrido[2,3-d]pyrimidine | 90° C. |
| 22 | 4-[2-(2-naphthalenyl)ethoxy]pyrido-[2,3-d]pyrimidine | 108° C. |
| 23 | 4-[2-(4-methoxyphenyl)ethoxy]-pyrido[2,3-d]pyrimidine | 109-110° C. |

| EXAMPLE NUMBER | COMPOUND | M.P. |
|---|---|---|
| 24 | 4-(4-fluorophenoxy)pyrido[3,4-d]pyrimidine | 212–214° C. |
| 25 | 4-[2-[4-phenylphenyl]ethoxy]pyrido[2,3-d]pyrimidine | 124–125° C. |
| 26 | 4-[2-[4-(t-butyl)phenyl]ethoxy]pyrido[3,4-d]pyrimidine | 59–60° C. |
| 27 | 4-[2-[4-(t-butyl)phenyl]-ethylamino]pyrido[2,3-d]pyrimidine | 209–211° C. |
| 28 | 4-[2-[4-(i-propyl)phenyl]ethylamino]pyrido[3,4-d]pyrimidine | 165–167° C. |
| 29 | 4-[2-[4-(t-butyl)phenyl]ethoxy]pyrido[3,2-d]pyrimidine | 55° C. |
| 30 | 4-[2-[4-(trifluoromethyl)phenyl]ethoxy]pyrido[2,3-d]pyrimidine | 65–67° C. |
| 31 | 4-(4-fluorophenoxy)pyrido[3,2-d]pyrimidine | 149–151° C. |
| 32 | 4-[2-[4-(trimethylsilyl)phenyl]ethoxy]pyrido[3,4-d]pyrimidine | 81° C. |
| 33 | 4-[2-(4-ethoxyphenyl)ethoxy]pyrido[3,4-d]pyrimidine | 87–88° C. |
| 34 | N-[2-(4-methoxyphenyl)ethyl]pyrido[2,3-d]pyrimidin-4-amine | 260–263° C. |
| 35 | N-[2-(4-methoxyphenyl)ethyl]pyrido[3,4-d]pyrimidin-4-amine | 153–155° C. |
| 36 | 4-(2-[1,1'-biphenyl]-4-ylethoxy)pyrido[3,4-d]pyrimidine | 137–138° C. |
| 37 | N-[2-[4-(t-butyl)phenyl]ethyl]pyrido[3,4-d]pyrimidin-4-amine | 138–163° C. |
| 38 | N-[2-(4-ethoxyphenyl)ethyl]pyrido[3,4-d]pyrimidin-4-amine | 174–176° C. |
| 39 | N-(4-phenylbutyl)pyrido[3,4-d]pyrimidin-4-amine | 60–75° C. |
| 40 | N-[2-(4-ethoxyphenyl)ethyl]pyrido[2,3-d]pyrimidin-4-amine | 220–222° C. |
| 41 | 4-[2-[4-(t-butyl)phenyl]ethoxy]pyrido[2,3-d]pyrimidine | 77–79° C. |
| 42 | N-[[3-trifluoromethyl)phenyl]methyl]pyrido[2,3-d]pyrimidin-4-amine | 202–201° C. |
| 43 | N-[[4-(trifluoromethoxy)phenyl]methyl]pyrido[2,3-d]pyrimidin-4-amine | 247–249° C. |
| 44 | N-[2-(4-methylphenyl)ethyl]pyrido[2,3-d]pyrimidin-4-amine | 260–264° C. |
| 45 | N-[2-(2-methoxyphenyl)ethyl]pyrido[2,3-d]pyrimidin-4-amine | 158–171° C. |
| 46 | N-(2-phenylethyl)pyrido[3,4-d]pyrimidin-4-amine | 134–137° C. |
| 47 | N-[4-(trifluoromethyl)phenyl]pyrido[2,3-d]pyrimidin-4-amine | 283–290° C. |
| 48 | 4-[[2-(4-methoxyphenyl)ethyl]amino]pyrido[3,2-d]pyrimidine | 120–122° C. |
| 49 | N-(2-phenylethyl)pyrido[3,2-d]pyrimidin-4-amine | 135–137° C. |
| 50 | N-[2-[4-(t-butyl)phenyl]ethyl]pyrido-[4,3-d]pyrimidin-4-amine | 157–158° C. |
| 51 | N-[2-(2-naphthyl)ethyl]pyrido[3,2-d]pyrimidin-4-amine | 140–143° C. |
| 52 | N-methyl-N-(2-phenylethyl)pyrido[2,3-d]pyrimidin-4-amine | 114–116° C. |
| 53 | N-methyl-N-[phenylmethyl]pyrido[2,3-d]pyrimidin-4-amine | 99–101° C. |
| 54 | 4-[2-(4-methylphenyl)ethoxy]pyrido[2,3-d]pyrimidine | 91–92° C. |
| 55 | 4-[2-[4-(t-butyl)phenyl]ethoxy]pteridine | 149° C. |
| 56 | 4-[2-(4-methylphenyl)ethoxy]pyrido[3,4-d]pyrimidine | 74–75° C. |
| 57 | 4-[2-(biphenyl)ethoxy]pyrido[3,2-d]pyrimidine | 83–84° C. |
| 58 | 4-[2-(4-methoxyphenyl)ethoxy]pyrido[3,4-d]pyrimidine | 80–81° C. |
| 59 | 4-[(4-methylphenyl)methoxy]pyrido[2,3-d]pyrimidine | 110–111° C. |
| 60 | 4-(2-cyclohexylethoxy)pyrido[2,3-d]pyrimidine | 72° C. |
| 61 | 4-[2-(phenyl)ethoxy]pyrido[3,4-d]pyrimidine | 77–78° C. |
| 62 | 4-[2-(4-chlorophenyl)ethoxy]pyrido[3,4-d]pyrimidine | 108–109° C. |
| 63 | 4-(3-phenylpropoxy)pyrido[2,3-d]pyrimidine | 34–36° C. |
| 64 | 4-[(2-phenylethyl)amino]pteridine | 159–160° C. |
| 65 | N-[2-(4-ethylphenyl)ethyl]pyrido[2,3-d]pyrimidin-4-amine | 218–220° C. |
| 66 | N-(2-ethoxyethyl)pyrido[2,3-d]pyrimidin-4-amine | N.A. |
| 67 | N-(2-methoxyethyl)pyrido[2,3-d]pyrimidin-4-amine | 190–193° C. |
| 68 | N-[2-(2-chloro-6-fluorophenyl)ethyl]pyrido[2,3-d]pyrimidin-4-amine | 248–251° C. |
| 69 | N-[3-(diethylamino)propyl]pyrido[2,3-d]pyrimidin-4-amine | 163–167° C. |
| 70 | N-[2-[4-(t-butyl)phenyl]ethyl]-4-pteridinamine | 147° C. |
| 71 | N-(phenylmethyl)pyrido[2,3-d]pyrimidin-4-amine | 258–260° C. |
| 72 | 4-[2-(2-methyl)ethoxy]pyrido[3,4-d]pyrimidine | 128–129° C. |

The procedures described in the following detailed examples are representative of the procedures used to prepare the compounds of the other examples.

Preparation 1

Pyrido[3,4-d]pyrimidin-4(3H)one

A mixture of 4 g of 3-amino-pyridine-4-carboxylic acid in 15 mL of formamide was heated in an oil bath to 160–180° C. After one hour the mixture was allowed to cool. Then, the mixture was slurried in 25 mL of water and filtered. The product was recrystallized from water. Yield 3.3 g. M.P. 317° C. (with sublimation).

Preparation 2

Pyrido[3,2-d]pyrimidin-4(3H)one

A mixture of 6.5 g of 3-amino-pyridine-2-carboxylic acid in 9 g of formamide was heated in an oil bath while stirring. The temperature was increased from 130° C. to 180° C. over a two hour period, then the mixture was allowed to cool. The mixture was then diluted with water. The solids were collected and washed with fresh water, then dried. Yield 4.6 g. M.P. 346–347° C.

Preparation 3

4-Chloropyrido[2,3-d]pyrimidine

A mixture of 17.8 g of Pyrido[2,3-d]pyrimidin4(3H-)one and 200 mL of POCl$_3$ was stirred under reflux for one hour. Excess POCl$_3$ was removed under vacuum, and then CH$_2$Cl$_2$, ice, and water were added. A black solid dissolved slowly. The organic layer was then separated, washed with aqueous NaHCO$_3$, and dried over Na$_2$SO$_4$. Solvent was then removed under vacuum to leave a yellow solid, which was recrystallized from toluene/hexane. M.P. 137° dec.

Preparation 4

4-[1'-(1,2,4-triazolyl)pyrido[2,3-d]-pyrimidine

A. A mixture of 28.5 g of Pyrido[2,3-d]-pyrimidin-4(3H)one and 40.1 g of 1,2,4-triazole in 500 mL of pyridine was stirred as 71.4 g of 4-chlorophenyl dichlorophosphate was added with modest cooling. The mixture was then stirred at room temperature. Then 2.5 L of CH$_2$Cl$_2$ was added, and the mixture was washed successively with 500 mL of water, 1 L of 2% HCl, and 500 mL of water, then dried over MgSO$_4$. Solvent was then evaporated, leaving a yellow solid, which was recrystallized from toluene/hexane to give 9.0 g first crop, M.P. 206–210° C., 5.7 g second crop, M.P. 218–220° C., 1.45 g third crop, M.P. 205–209° C.

B. The title compound was also made by mixing 1.47 g of pyrido[2,3-d]pyrimidin-4(3H)one and 2.07 g of 1,2,4-triazole in 50 mL of pyridine and adding 1.12 mL of $POCl_3$ while stirring the mixture at room temperature. After stirring the mixture overnight, 500 mL of $CH_2Cl_2$ was added, and the mixture was washed successively with 500 mL of 2% HCl and 500 mL of water, and then dried over $MgSO_4$. Solvent was evaporated under vacuum to leave 0.4 of yellow solid, which was recrystallized from toluene/hexane. M.P. 217–219° C.

EXAMPLE 2

4-[2-[4-(i-propyl)phenyl]ethylamino]-pyrido[2,3-d]-pyrimidine

A mixture consisting of 1.98 g (.01 mole) of 4-[1'-(1,2,4-triazolyl)]pyrido[2,3-d]pyrimidine, 1.63 g (0.01 mole) of 2-[4-(i-propyl)phenyl]ethylamine, and 50 mL of $CHCl_3$ was stirred at reflux for two hours. Then 1.01 g (0.01 mole) of triethyl amine was added, and the mixture was refluxed for four hours. After washing the mixture with water, the $CHCl_3$ layer was dried over $MgSO_4$. The $CHCl_3$ was removed using a vacuum and the product was recrystallized from $EtOH/H_2O$. Yield 1.5 g. This product was recrystallized from ethyl acetate. M.P. 200–203° C.

EXAMPLE 3

4-[2-(4-chlorophenyl)ethoxy]pyrido[2,3-d]pyrimidine

A mixture consisting of 1.48 g (7.5 mmole) of 4-[1'(1,2,4-triazolyl)-pyrido[2,3-d]pyrimidine, 1.20 g of 2-(4-chlorophenyl)ethanol (7.5 mmole), and 50 mL of toluene which had been treated with dry HCl gas was stirred at room temperature, heated gently for about one and one half hours, then cooled. TLC indicated that the reaction was not complete, so additional alcohol was added and the mixture was warmed. After cooling the mixture, it was diluted with water and made basic with 1.0 N NaOH. The product was extracted from the mixture into toluene, which was then washed with saturated brine, filtered through phase separating paper, and concentrated in vacuo. The oily residue that crystallized was chromatographed (silica gel, $CH_2Cl_2 \rightarrow 70\%$ $CH_2Cl_2/30\%$ EtOAc). The fractions containing the major product were combined, and the product crystallized. The product was recrystallized from $CH_2Cl_2$/petroleum ether. Yield 1.05 g. M.P. 126–128° C.

EXAMPLE 26

4-[2-[4-(t-butyl)phenyl]ethoxy]pyrido[3,4-d]pyrimidine

To a suspension of 300 mg of 60% NaH in 15 mL of DMF was added 1.33 g of 2-[4-(t-butyl)phenyl]ethanol. The mixture was stirred at room temperature for 30 minutes. The 1.48 g of 4-[1'-(1,2,4-triazolyl)pyrido[3,4-d]pyrimidine was added and the mixture was stirred at room temperature overnight. Solvent was then removed in vacuo, azeotroping with xylene. The residue was diluted with water and the pH was adjusted to neutral by adding dilute HCl. The product was extracted into $CH_2Cl_2$, which was then washed with brine, dried over $Na_2SO_4$, filtered, and concentrated. The residue was adsorbed onto silica gel and chromatographed, eluting with $CH_2Cl_2$ to 75/25 $CH_2Cl_2$/EtOAc. Fractions containing the major product were combined to give a thick oil which crystallized from petroleum ether. Yield 1.4 g. M.P. 59–60° C.

EXAMPLE 41

4-[2-[4-(t-butyl)phenyl]ethoxy]pyrido[2,3-d]pyrimidine

A mixture consisting of 1.86 g (0.011 mole) of 4-chloropyrido-[2,3-d]pyrimidine, 2.0 g (0.011 mole) of 2-[4-(t-butyl)phenyl]ethanol, and 40 mL of toluene containing a little HCl gas was stirred at room temperature. The mixture was then cooled, and a yellow solid was collected. This was washed with hexane, then partitioned between 1N NaOH and $CH_2Cl_2$. The $CH_2Cl_2$ layer was dried over $MgSO_4$, then the solvent was removed under vacuum to leave a yellow solid, which was recrystallized from hexane. Yield 2.5 g. M.P. 77–79° C.

EXAMPLE 50

4-[2-[4-(t-butyl)phenyl]ethylamino]pyrido-[4,3-d]pyrimidine

A mixture consisting of 0.45 g of pyrido-[4,3-d]pyrimidine-4-ol, 0.53 g of 2-[4-(t-butyl)phenyl]ethylamine, about 40 mg of $(NH_4)_2SO_4$ in 4 mL of hexamethyldisilazane was refluxed for about five hours. The mixture was then cooled and excess disilazane was removed in vacuo. The residue was dissolved in $CH_2Cl_2$, and the solution was washed with water and filtered through phase separating paper. Evaporated the $CH_2Cl_2$ and adsorbed the residue onto silica gel, which was applied to a thin silica pad and eluted with $CH_2Cl_2 \rightarrow 50\%$ EtOAc/50% $CH_2Cl_2$ EtOAc. Fractions containing the major product were combined and the product which crystallized was recrystallized from hexane/EtOAc. Yield 0.2 g. M.P. 157–158° C.

EXAMPLE 55

4-[2-[4-(t-butyl)phenyl]ethoxy]pteridine

To a suspension of 2 g of 4-hydroxypteridine in 20 mL of $CH_2Cl_2$ under nitrogen was added 1.2 g of 25 pyridine. The mixture was cooled to -30° C and over a 15 minute period a solution of 4.82 g of triphenyl phosphite in $CH_2Cl_2$ was added simultaneously with addition of chlorine gas. The mixture was stirred for one and one half hours while maintaining the temperature at −15 to −20° C. The mixture was then allowed to warm to 10° C., and a solution of 2.67 g of 2-[4-(t-butyl)-phenyl]ethanol in $CH_2Cl_2$ was added. The resulting mixture was refluxed for 45 minutes, then cooled and diluted into toluene. The toluene solution was washed with dilute base, then filtered through phase separating paper and concentrated in vacuo. The resulting bluish oil was adsorbed onto silica gel and chromatographed (silica gel, $CH_2Cl_2 \rightarrow 80\%$ $CH_2Cl_2$, 20% EtOAc). Fractions containing the major product were combined. The product was then recrystallized from petroleum ether/$CH_2Cl_2$. Yield 60 mg. M.P. 149° C.

Fungicide Utility

The compounds of the present invention have been found to control fungi, particularly plant pathogens. When employed in the treatment of plant fungal diseases, the compounds are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 4 lb/A. The compounds of the invention may also be used to protect stored grain and other non-plant loci from fungal infestation.

Greenhouse Tests

The following experiments were performed in the laboratory to determine the fungicidal efficacy of the compounds of the invention.

This screen was used to evaluate the efficacy of the present compounds against a variety of different organisms that cause plant diseases.

The test compounds were formulated for application by dissolving 50 mg of the compound into 1.25 ml of solvent. The solvent was prepared by mixing 50 ml of "Tween 20" (polyoxyethylene (20) sorbitan monolaurate emulsifier) with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Following Table | Host |
|---|---|---|
| *Erysiphe qraminis tritici* (powdery mildew) | POWD MDEW | wheat |
| *Pyricularia oryzae* (rice blast) | RICE BLAS | rice |
| *Puccinia recondita tritici* (leaf rust) | LEAF RUST | wheat |
| *Botrytis cinerea* (gray mold) | GRAY MOLD | grape berries |
| *Pseudoperonospora cubensis* (downy mildew) | DOWN MDEW | squash |
| *Cercospora beticola* (leaf spot) | LEAF SPOT | sugar beet |
| *Venturia inaequalis* (apple scab) | APPL SCAB | apple seedling |
| *Septoria tritici* (leaf blotch) | LEAF BLOT | wheat |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2-4 hours.

The following Table presents the activity of typical compounds of the present invention when evaluated in this experiment. The effectiveness of test compounds in controlling disease was rated using the following scale.
0 = not tested against specific organism
− = 0-19% control at 400 ppm
+ = 20-89% control at 400 ppm
+ + = 90-100% control at 400 ppm
+ + + = 90-100% control at ppm

| | PLANT PATHOLOGY SCREEN | | | | |
|---|---|---|---|---|---|
| EXAMPLE NUMBER | POWD MDEW | RICE BLAST | LEAF RUST | GRAY MOLD | DOWN MDEW |
| 1 | − | − | − | − | − |
| 2 | − | − | +++ | − | +++ |
| 3 | + | +++ | +++ | − | +++ |
| 4 | − | ++ | + | − | + |
| 5 | +++ | +++ | +++ | + | +++ |
| 6 | + | − | − | − | + |
| 7 | + | − | ++ | − | +++ |
| 8 | − | − | +++ | − | +++ |
| 9 | − | − | ++ | − | + |
| 10 | ++ | − | +++ | − | +++ |
| 11 | ++ | − | +++ | − | +++ |
| 12 | − | − | ++ | − | +++ |
| 13 | − | − | +++ | − | +++ |
| 14 | − | − | + | − | +++ |
| 15 | + | − | +++ | − | +++ |
| 16 | − | − | + | − | − |
| 17 | +++ | +++ | +++ | − | +++ |
| 18 | − | ++ | +++ | − | +++ |
| 19 | − | − | + | − | − |
| 20 | − | − | − | − | + |
| 21 | +++ | − | +++ | − | +++ |
| 22 | +++ | − | +++ | − | +++ |
| 23 | − | +++ | +++ | − | +++ |
| 24 | − | − | − | − | − |
| 25 | +++ | +++ | +++ | − | +++ |
| 26 | +++ | +++ | +++ | − | +++ |
| 27 | − | + | +++ | − | +++ |
| 28 | +++ | +++ | +++ | − | +++ |
| 29 | ++ | ++ | ++ | − | +++ |
| 30 | +++ | +++ | +++ | − | +++ |
| 31 | − | − | − | − | − |
| 32 | ++ | ++ | ++ | − | ++ |
| 33 | ++ | − | ++ | − | ++ |
| 34 | − | + | ++ | − | ++ |
| 35 | ++ | +++ | +++ | − | +++ |
| 36 | − | ++ | + | − | +++ |
| 37 | ++ | +++ | +++ | − | +++ |
| 38 | ++ | ++ | +++ | − | +++ |
| 39 | +++ | ++ | +++ | − | +++ |
| 40 | + | + | +++ | − | ++ |
| 41 | +++ | +++ | +++ | − | +++ |
| 43 | − | − | ++ | − | + |
| 44 | − | − | + | − | ++ |
| 45 | − | − | ++ | − | ++ |
| 46 | ++ | − | ++ | − | ++ |
| 47 | − | − | − | − | ++ |
| 48 | ++ | ++ | ++ | − | ++ |
| 49 | + | − | ++ | − | ++ |
| 50 | − | − | ++ | − | ++ |
| 51 | +++ | + | +++ | − | +++ |
| 52 | ++ | − | ++ | − | ++ |
| 53 | − | − | + | 0 | + |
| 54 | ++ | − | ++ | 0 | ++ |
| 55 | − | − | + | − | +++ |
| 61 | ++ | ++ | ++ | − | ++ |
| 65 | − | − | +++ | − | +++ |
| 67 | − | − | − | 0 | ++ |
| 72 | + | ++ | +++ | − | +++ |

Combinations

Fungal disease pathogens are known to develop resistance to fungicides. When strains resistant to a fungicide do develop, it becomes necessary to apply larger and larger amounts of the fungicide to obtain desired results. To retard the development of resistance to new fungicides, it is desirable to apply the new fungicides in combination with other fungicides. Use of a combination product also permits the product's spectrum of activity to be adjusted.

Accordingly, another aspect of the invention is a fungicidal combination comprising at least 1% by weight of a compound of formula (1) in combination with a second fungicide.

Contemplated classes of fungicides from which the second fungicide may be selected include:

1) N-substituted azoles, for example propiconazole, triademefon, flusilazol, diniconazole, ethyltrianol, myclobutanil, and prochloraz;
2) pyrimidines, such as fenarimol and nuarimol;
3) morpholines, such as fenpropimorph and tridemorph;
4) piperazines, such as triforine; and
5) pyridines, such as pyrifenox.

Fungicides in these five classes all function by inhibiting sterol biosynthesis. Additional classes of contemplated fungicides, which have other mechanisms of action include:

6) dithiocarbamates, such as maneb and mancozeb;
7) phthalimides, such as captafol;
8) isophthalonitrites, such as chlorothalonil;
9) dicarboximides, such as iprodione;
10) benzimidazoles, such as benomyl and carbendazim;
11) 2-aminopyrimidines, such as ethirimol;
12) carboxamides, such as carboxin;
13) dinitrophenols, such as dinocap; and
14) acylalanines, such as metalaxyl.

The fungicide combinations of the invention contain at least 1%, ordinarily 20 to 80%, and more typically 50 to 75% by weight of a compound of formula (1).

Insecticide and Miticide Utility

The compounds of the invention are also useful for the control of insects and mites. Therefore, the present invention also is directed to a method for inhibiting an insect or mite which comprises applying to a locus of the insect or mite an insect- or mite-inhibiting amount of a compound of formula (1).

The compounds of the invention show activity against a number of insects and mites. More specifically, the compounds show activity against melon aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm.

Representative mite species with which it is contemplated that the present invention can be practiced include those listed below.

| FAMILY | SCIENTIFIC NAME | COMMON NAME |
|---|---|---|
| ACARIDAE | Aleurobius farinae | |
| | Rhizoglyphus echinopus | Bulb mite |
| | Rhizoglyphus elongatus | |
| | Rhizoglyphus rhizophagus | |
| | Rhizoglyphus sagittatae | |
| | Rhizoglyphus tarsalis | |
| ERIOPHYIDAE | Abacarus farinae | Grain rust mite |
| | Aceria brachytarsus | |
| | Acalitus essigi | Redberry mite |
| | Acera ficus | |
| | Aceria fraaxinivorus | |
| | Aceria granati | |
| | Aceria parapopuli | |
| | Eriophyes sheldoni | Citrus bud mite |
| | Aceria tulipae | |
| | Aculus carnutus | Peach silver mite |
| | Aculus schlechtendali | Apple rust mite |
| | Colomerus vitis | Grape erineum mite |
| | Eriophyes convolvens | |
| | Eriophyes insidiosus | |
| | Eriophyes malifoliae | |
| | Eriophyes padi | |
| | Eriophyes pruni | |
| | Epitrimerus pyri | Pear leaf blister mite |
| | Eriophyes ramosus | |
| | Eriophyes sheldoni | Citrus bud mite |
| | Eriophyes ribis | |
| | Phyllocoptes gracilis | Dryberry mite |
| | Phyllocoptruta oleivora | Citrus rust mite |
| | Phytoptus ribis | |
| | Trisetacus pini | |
| | Vasates amygdalina | |
| | Vasates eurynotus | |
| | Vasates quadripedes | Maple bladdergall mite |
| | Vasates schlechtendali | |
| EUPODIDAE | Penthaleus major | Winter grain mite |
| | Linopodes spp. | |
| NALEPELLIDAE | Phylocoptella avellanae | Filbert bud mite |
| PENTHALEIDAE | Halotydeus destrustor | |
| PYEMOTIDAE | Pyemotes tritici | Straw itch mite |
| | Siteroptes cerealium | |
| TARSONEMIDAE | Polyphagotarsonemus latus | Broad mite |
| | Steneotarsonemus pallidus | Cyclamen mite |
| TENUIPALPIDAE | Brevipalpus californicus | |
| | Brevipalpus obovatus | Privet mite |
| | Brevipalpus lewisi | Citrus flat mite |

-continued

| FAMILY | SCIENTIFIC NAME | COMMON NAME |
|---|---|---|
| | Dolichotetranychus floridanus | Pineapple flase spider mite |
| | Tenuipalpes granati | |
| | Tenuipalpes pacificus | |
| TETRANYCHIDAE | Bryobia arborea | |
| | Bryobia practiosa | Clover mite |
| | Bryobia rubrioculus | Brown mite |
| | Eotetranychus coryli | |
| | Eotetranychus hicoriae | Pecan deaf scorch mite |
| | Eotetranychus lewisi | |
| | Eotetranychus sexmaculatus | Sixspotted spider mite |
| | Eotetranychus willametti | |
| | Eotetranychus banksi | Texas citrus mite |
| | Oligonychus ilicis | Southern red mite |
| | Oligonychus pratensis | Banks grass mite |
| | Oligonychus ununguis | Spruce spider mite |
| | Panonychus citri | Citrus red mite |
| | Panonychus ulmi | European red mite |
| | Paratetranychus modestus | |
| | Paratetranychus pratensis | |
| | Paratetranychus viridis | |
| | Petrobia latens | Brown wheat mite |
| | Schizotetranychus celarius | Bamboo spider mite |
| | Schizotetranychus pratensis | |
| | Tetranychus canadensis | Fourspotted spider mite |
| | Tetranychus cinnabarinus | Carmine spider mite |
| | Tetranvchus mcdanieli | McDaniel spider mite |
| | Tetranychus pacificus | Pacific spider mite |
| | Tetranychus schoenei | Schoene spider mite |
| | Tetranychus urticae | Twospotted spider mite |
| | Tetranychus turkestani | Strawberry spider mite |
| | Tetranychus desertorum | Desert spider mite |

The compounds are useful for reducing populations of insects and mites, and are used in a method of inhibiting an insect or mite population which comprises applying to a locus of the insect or arachnid an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts, which the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites; or a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm active compound is used.

In a preferred embodiment, the present invention is directed to a method for inhibiting a mite which comprises applying to a plant an effective mite-inactivating amount of a compound of formula (1) in accordance with the present invention.

MITE/INSECT SCREEN

The compounds of Examples 1-10 were tested for miticidal and insecticidal activity in the following mite-/insect screen.

Each test compound was formulated by dissolving the compound in acetone/alcohol (50:50) mixture containing 23 g of "TOXIMUL R" (sulfonate/nonionic emulsifier blend) and 13 g of "TOXIMUL S" (sulfonate/nonionic emulsifier blend) per liter. These mixtures were then diluted with water to give the indicated concentrations.

Twospotted spider mites (*Tetranychus urticae* Koch) and melon aphids (*Aphis gossypii* Glover) were introduced on squash cotyledons and allowed to establish on both leaf surfaces. Other plants in the same treatment pot were left uninfested. The leaves were then sprayed with 5 ml of test solution using a DeVilbiss atomizing sprayer at 10 psi. Both surfaces of the leaves were covered until runoff, and then allowed to dry for one hour. Two uninfested leaves were then excised and placed into a Petri dish containing larval southern armyworm (*Spodopetra eridania* Cramer).

Activity on Southern corn rootworm (*Diabrotica undecimpuctata howardi* Barber) was evaluated by adding two ml of tap water, a presoaked corn seed, and 15 g of dry sandy soil to a one ounce plastic container. The soil was treated with 1 mL of test solution containing a predetermined concentration of test compound. After six to 12 hours of drying, five 2-3 instar corn rootworm larvae were added to the individual cups, which were then capped and held at 23° C.

After standard exposure periods, percent mortality and phytotoxicity were evaluated. Results for the compounds found to be active are reported in the following table. The remaining compounds showed no activity. The following abbreviations are used in the following table:

CRW refers to corn rootworm
SAW refers to Southern armyworm
SM refers to twospotted spider mites
MA refers to melon aphids.

MITE AND INSECT SCREEN

| EXAMPLE NUMBER | RATE PPM | SAW RESULTS % | SM RESULTS % | MA RESULTS % |
|---|---|---|---|---|
| 1 | 400 | 0 | 0 | 0 |
| 2 | 200 | 0 | 0 | 0 |
|   | 400 | 80 | 0 | 0 |
| 3 | 200 | 0 | 0 | 0 |
|   | 400 | 0 | 0 | 0 |
| 4 | 200 | 0 | 0 | 0 |
|   | 400 | 0 | 0 | 0 |
| 5 | 200 | 0 | 100 | 90 |
|   | 400 | 0 | 100 | 100 |
| 6 | 400 | 0 | 0 | 0 |
| 7 | 200 | 0 | 0 | 90 |
|   | 400 | 0 | 0 | 0 |
| 8 | 200 | 0 | 0 | 0 |
|   | 400 | 0 | 0 | 0 |
| 9 | 200 | 80 | 0 | 0 |
|   | 400 | 70 | 0 | 0 |
| 10 | 200 | 0 | 90 | 90 |
|    | 200 | 0 | 80 | 100 |
|    | 400 | 0 | 100 | 100 |
| 11 | 200 | 0 | 100 | 100 |
|    | 400 | 0 | 100 | 100 |
| 12 | 200 | 0 | 0 | 0 |
|    | 400 | 0 | 0 | 0 |
| 13 | 200 | 60 | 0 | 0 |
|    | 400 | 0 | 0 | 0 |
| 14 | 200 | 0 | 0 | 50 |
|    | 400 | 0 | 0 | 0 |
| 15 | 200 | 0 | 0 | 0 |
|    | 400 | 0 | 80 | 80 |
| 16 | 200 | 80 | 0 | 0 |
|    | 400 | 0 | 0 | 0 |
| 17 | 200 | 0 | 80 | 80 |
|    | 400 | 0 | 60 | 80 |
| 18 | 200 | 0 | 30 | 80 |
|    | 400 | 0 | 90 | 90 |
| 19 | 200 | 0 | 0 | 0 |
|    | 400 | 0 | 0 | 0 |
| 20 | 200 | 0 | 0 | 0 |
|    | 400 | 0 | 0 | 0 |
| 21 | 200 | 70 | 100 | 100 |
|    | 400 | 0 | 100 | 60 |
| 22 | 200 | 90 | 100 | 100 |
|    | 400 | 0 | 60 | 80 |
| 23 | 200 | 0 | 0 | 90 |
|    | 400 | 0 | 40 | 80 |
| 24 | 400 | 0 | 0 | 0 |
| 25 | 200 | 80 | 50 | 60 |
|    | 400 | 0 | 0 | 0 |
| 26 | 200 | 0 | 100 | 80 |
|    | 400 | 0 | 0 | 0 |
| 27 | 200 | 0 | 0 | 20 |
|    | 400 | 0 | 0 | 0 |
| 28 | 200 | 0 | 20 | 30 |
|    | 400 | 0 | 0 | 0 |
| 29 | 200 | 0 | 100 | 90 |
|    | 400 | 0 | 80 | 80 |
| 30 | 200 | 0 | 100 | 100 |
|    | 400 | 0 | 100 | 100 |
| 31 | 400 | 0 | 0 | 0 |
| 32 | 200 | 60 | 100 | 90 |
|    | 400 | 0 | 0 | 0 |
| 33 | 200 | 0 | 0 | 0 |
|    | 400 | 0 | 0 | 0 |
| 34 | 200 | 60 | 0 | 0 |
|    | 400 | 0 | 0 | 0 |
| 35 | 200 | 0 | 0 | 60 |
|    | 400 | 0 | 0 | 0 |
| 36 | 200 | 0 | 0 | 0 |
|    | 400 | 0 | 0 | 0 |
| 37 | 200 | 0 | 0 | 0 |
|    | 400 | 0 | 0 | 0 |
| 38 | 200 | 20 | 0 | 0 |
| 39 | 400 | 20 | 0 | 0 |
|    | 200 | 0 | 80 | 0 |
|    | 400 | 0 | 0 | 0 |
| 40 | 200 | 20 | 0 | 0 |
|    | 400 | 0 | 0 | 0 |
| 41 | 200 | 0 | 100 | 100 |
|    | 400 | 0 | 100 | 100 |
| 44 | 200 | 0 | 0 | 0 |
|    | 400 | 40 | 0 | 0 |
| 45 | 200 | 0 | 0 | 0 |
|    | 400 | 0 | 0 | 0 |
| 46 | 400 | 0 | 0 | 0 |
| 47 | 200 | 0 | 20 | 90 |
|    | 400 | 0 | 0 | 0 |
| 48 | 200 | 0 | 80 | 60 |
|    | 400 | 0 | 0 | 0 |
| 49 | 200 | 0 | 0 | 0 |
|    | 400 | 0 | 0 | 0 |
| 50 | 200 | 0 | 90 | 70 |
|    | 400 | 0 | 0 | 0 |
| 51 | 200 | 50 | 80 | 80 |
|    | 400 | 40 | 0 | 0 |
| 52 | 200 | 0 | 0 | 0 |
|    | 400 | 0 | 100 | 100 |
| 53 | 400 | 0 | 0 | 0 |
| 54 | 400 | 0 | 100 | 100 |
| 55 | 400 | 0 | 0 | 0 |
| 57 | 200 | 0 | 90 | 90 |
|    | 400 | 0 | 80 | 100 |
| 61 | 400 | 0 | 0 | N.A. |
| 64 | 400 | 0 | 0 | 0 |
| 65 | 200 | 90 | 0 | 0 |
|    | 400 | 100 | 0 | 0 |
| 67 | 400 | 0 | 0 | 100 |
| 68 | 400 | 0 | 0 | 0 |
| 72 | 200 | 0 | 0 | 0 |
|    | 400 | 0 | 0 | 0 |

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and non-ionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional non-ionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

| A. 0.75 Emulsifiable Concentrate | |
|---|---|
| Compound of Example 25 | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |
| B. 1.5 Emulsifiable Concentrate | |
| Compound of Example 25 | 18.50% |
| "TOXIMUL D" | 2.50% |
| "TOXIMUL H" | 2.50% |
| "EXXON 200" | 76.50% |
| C. 0.75 Emulsifiable Concentrate | |
| Compound of Example 41 | 9.38% |
| "TOXIMUL D" | 2.50% |
| "TOXIMUL H" | 2.50% |
| "EXXON 200" | 85.62% |
| D. 1.0 Emulsifiable Concentrate | |
| Compound of Example 41 | 12.50% |
| N-methylpyrrolidone | 25.00% |
| "TOXIMUL D" | 2.50% |
| "TOXIMUL H" | 2.50% |
| "EXXON 200" | 57.50% |
| E. 1.0 Aqueous Suspension | |
| Compound of Example 25 | 12.00% |
| "PLURONIC P-103" (block copolymer of propylene oxide and ethylene oxide, surfactant) | 1.50% |
| "PROXEL GXL" (biocide/preservative) | .05% |
| "AF-100" (silicon based antifoam agent) | .20% |

-continued

| | |
|---|---|
| "REAX 88B" (lignosulfonate dispersing agent) | 1.00% |
| propylene glycol | 10.00% |
| veegum | .75% |
| xanthan | .25% |
| water | 74.25% |
| F. 1.0 Aqueous Suspension | |
| Compound of Example 25 | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |
| G. 1.0 Aqueous Suspension | |
| Compound of Example 41 | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |
| H. Wettable Powder | |
| Compound of Example 25 | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |
| I. Aqueous Suspension | |
| Compound of Example 25 | 12.40% |
| "TERGITOL 158-7" | 5.00% |
| "ZEOSYL 200" | 1.00% |
| "AF-100" | 0.20% |
| "POLYFON H" | 0.50% |
| 2% xanthan solution | 10.00% |
| tap water | 70.90% |
| J. Emulsifiable Concentrate | |
| Compound of Example 25 | 12.40% |
| "TOXIMUL D" | 2.50% |
| "TOXIMUL H" | 2.50% |
| "EXXON 200" | 82.60% |
| K. Wettable Powder | |
| Compound of Example 41 | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |
| L. Emulsifiable Concentrate | |
| Compound of Example 25 | 6.19% |
| "TOXIMUL H" | 3.60% |
| "TOXIMUL D" | 0.40% |
| "EXXON 200" | 89.81% |
| M. Wettable Powder | |
| Compound of Example 25 | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |
| N. Aqueous Suspension | |
| Compound of Example 41 | 12.40% |
| "TERGITOL 158-7" | 5.00% |
| "ZEOSYL 200" | 1.00% |
| "POLYFON H" | 0.50% |
| "AF-100" | 0.20% |
| xanthan solution (2%) | 10.00% |
| tap water | 70.90% |

We claim:

1. A fungicidal composition comprising a compound of formula (1):

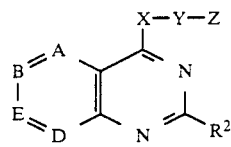

wherein or A, C, and D are N and B is $CR^1$;

a) A is N and B, E, and D are $CR^1$;
b) B is N and E, E, and D are $CR^1$;
c) E is N and A, B, and D are $CR^1$;
d) D is N and A, B, and E are $CR^1$;
e) A and D are N and B and E are $CR^1$;
f) B and D are N and A and E are $CR^1$;
g) E and D are N and A and B are $CR^1$;
h) A and E are N and B and D are $CR^1$;
i) A and B are N and E and D are $CR^1$;
j) A and B are N and E and D are $CR^1$;
k) A, E, and D are N and B is $CR^1$;

where $R^1$ and $R^2$ are independently H, halo, $(C_1-C_4)$ alkyl, $(C_3-C_4)$ branched alkyl, $(C_1-C_4)$ alkoxy, halo $(C_1-C_4$ alkyl, phenyl, or substituted phenyl;

X is O, S, SO, $SO_2$, $NR^3$, or $CR^4R^5$, where $R^3$ is H, $(C_1-C_4)$ alkyl, or $(C_1-C_4)$ acyl, and $R^4$ and $R^5$ are independently H, $(C_1-C_4)$ acyl, $(C_1-C_4)$ alkyl, $(C_2-C_4)$ alkenyl or -alkynyl, CN, or OH, or $R^4$ and $R^5$ combine to form a carbocyclic ring containing four to six carbon atoms;

Y is a bond or an alkylene chain one to six carbon atoms long, optionally including a carbocyclic ring, and optionally including a hetero atom selected from O, $NR^3$, S, SO, $SO_2$, or $SiR^{20}R^{21}$, where $R^3$ is as defined above and $R^{20}$ and $R^{21}$ are independently $(C_1-C_4)$ alkyl, $(C_3-C_4)$ branched alkyl, phenyl, or substituted phenyl, and optionally substituted with $(C_1-C_4)$ alkyl, $(C_2-C_4)$ alkenyl or -alkynyl, branched $(C_3-C_7)$ alkyl, $(C_3-C_7)$ cycloalkyl or -cycloalkenyl, halo, hydroxy, or acetyl, and Z is (a) a $(C_1-C_{12})$ saturated or unsaturated hydrocarbon chain, straight chain or branched optionally including a hetero atom selected from O, S, SO, $SO_2$, or $SiR^{20}R^{21}$, where $R^{20}$ and $R^{21}$ are as defined above, and optionally substituted with halo, halo $(C_1-C_4)$ alkoxy, hydroxy, $(C_3-C_8)$ cycloalkyl or cycloalkenyl, or $(C_1-C_4)$ acyl;

(b) $(C_3-C_8)$ cycloalkyl or cycloalkenyl, optionally substituted with $(C_1-C_4)$ alkyl, $(C_1-C_4)$ alkoxy, halo $(C_1-C_4)$ alkyl, halo $(C_1-C_4)$ alkoxy, halo, hydroxy, or $(C_1-C_4)$ acyl;

(c) a phenyl group of the formula (2)

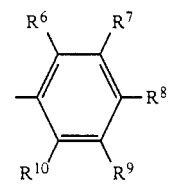

where $R^6$ to $R^{10}$ are independently H, halo, I, $(C_1-C_{10})$ alkyl, $(C_3-C_8)$ alkenyl or -alkynyl, branched $(C_3-C_6)$ alkyl, -alkenyl, or -alkynyl, $(C_3-C_8)$ cycloalkyl or -cycloalkenyl, halo $(C_1-C_7)$ alkyl, $(C_1-C_7)$ alkoxy, $(C_1-C_7)$ alkylthio, halo $(C_1-C_7)$ alkoxy, phenoxy, substituted phenoxy, phenylthio, substituted phenylthio, phenyl, substituted phenyl, $NO_2$, acetoxy, OH, CN, $SiR^{11}R^{12}R^{13}$, $OSiR^{11}R^{12}R^{13}$, $NR^{14}R^{15}$, $S(O)R^{16}$, or $SO_2R^{17}$ where $R^{11}$, $R^{12}$, and $R^{13}$ are independently $(C_1-C_4)$ alkyl, $(C_3-C_4)$ branched alkyl, phenyl, or substituted phenyl, $R^{14}$ and $R^{15}$ are independently H, $(C_1-C_4)$ alkyl, or $(C_1-C_4)$ acyl, and $R^{16}$ and $R^{17}$ are $(C_1-C_{10})$ alkyl, phenyl, or substituted phenyl;

(d) a furyl group of formula (3)

$$\text{(3)}$$

where $R^{18}$ is H, halo, halomethyl, CN, $NO_2$, $(C_1-C_4)$ alkyl, $(C_3-C_4)$ branched alkyl, phenyl, or $(C_1-C_4)$ alkoxy;

(e) a thienyl group of the formula (4)

$$\text{(4)}$$

where $R^{18}$ is as defined in paragraph (d);

(f) a group of formula (5) or (6)

$$\text{(5)}$$

$$\text{(6)}$$

where $R^{18}$ is as defined in paragraph (d), J is N or CH, and G is O, $NR^{19}$, or S, provided that if J is not N then G is $NR^{19}$, where $R^{19}$ is H, $(C_1-C_4)$ alkyl, $(C_1-C_4)$ acyl, phenylsulfonyl, or substituted phenylsulfonyl;

(g) a group selected from
  optionally substituted naphthyl, dihydronaphthyl, tetrahydronaphthyl, and decahydronaphthyl;
  optionally substituted pyridyl;
  optionally substituted indolyl;
  and 1,3-benzodioxolyl;
  or an acid addition salt of a compound of formula (1);
provided that the following compounds are excluded:
1) pyrido[2,3-d]pyrimidines of formula (1) wherein X and $NR^3$ in combination with a phytologically acceptable carrier.

2. A plant fungicidal method which comprises applying to the locus of a plant pathogen a disease inhibiting and phytologically acceptable amount of a compound of formula (1) as defined in claim 1.

3. A composition of claim 1 wherein the compound of formula (1) is one wherein X is O.

4. A composition of claim 3 wherein the compound of formula (1) is one wherein A, G, and E are $CR^1$ and D is N.

5. A composition of claim 4 wherein the compound of formula (1) is one wherein at least two of A, B, and E are CH.

6. A composition of claim 3 wherein the compound of formula (1) is one wherein Y is a chain at least two atoms long.

7. A composition of claim 3 wherein the compound of formula (1) is one wherein Z is a group of formula (2).

8. A composition of claim 7 wherein the compound of formula (1) is one wherein at least one of $R^6$ to $R^{10}$ is branched $(C_3-C_6)$ alkyl, halo $(C_1-C_4)$ alkyl, halo $(C_1-C_4)$ alkoxy, phenyl, substituted phenyl, phenoxy, substituted phenoxy, phenylthio, substituted phenylthio, $SiR^{11}R^{12}R^{13}$, or $OSiR^{11}R^{12}R^{13}$.

9. A composition of claim 1 wherein the compound of formula (1) is 4-[2-[4-(t-butyl)phenyl]ethoxy]pyrido[2,3-d]pyrimidine.

10. A composition of claim 1 wherein the compound of formula (1) is 4-[2-(1,1'-biphenyl)-4ylethoxy]-pyrido[2,3-d]pyrimidine.

11. A composition of claim 1 wherein the compound of formula (1) is 4-[2-(4-ethoxyphenyl)ethoxy]-pyrido[2,3-d]pyrimidine.

12. A composition of claim 1 wherein the compound of formula (1) is one wherein X is $NR^3$.

13. A composition of claim 12 wherein the compound of formula (1) is one wherein X is NH.

14. A composition of claim 12 wherein the compound of formula (1) is one wherein Z is a group of formula (2).

15. A composition of claim 14 wherein the compound of formula (1) is one wherein at least one of $R^6$ to $R^{10}$ is branched $(C_3-C_6)$ alkyl, halo $(C_1-C_4)$ alkyl, halo $(C_1-C_4)$ alkoxy, phenyl, substituted phenyl, phenoxy, substituted phenoxy, phenylthio, substituted phenylthio, $SiR^{11}R^{12}R^{13}$, or $OSiR^{11}R^{12}R^{13}$.

16. A composition of claim 12 wherein the compound of formula (1) is one wherein Y is a chain at least two atoms long.

17. A composition of claim 1 wherein the compound of formula (1) is one wherein Y is a chain at least two atoms long.

18. A composition of claim 1 wherein the compound of formula (1) is one wherein Z is a group of formula (2).

19. A composition of claim 1 wherein the compound of formula (1) is one wherein at least one of $R^6$ to $R^{10}$ is branched $(C_3-C_6)$ alkyl, halo $(C_1-C_4)$ alkyl, halo $(C_1-C_4)$ alkoxy, phenyl, substituted phenyl, phenoxy, substituted phenoxy, phenylthio, substituted phenylthio, $SiR^{11}R^{12}R^{13}$, or $OSiR^{11}R^{12}R^{13}$.

20. A composition of claim 1 wherein the compound of formula (1) is one of the formula (1a)

$$\text{(1a)}$$

wherein A, B, and E are $CR^1$ and X, Y, $R^2$, $R^6$, $R^7$, $R^8$, $R^9$, and $R^{10}$ are as defined in claim 1.

21. A composition of claim 1 wherein the compound of formula (1) is one wherein
  a) A is N and B, E, and D are $CR^1$;
  b) B is N and A, E, and D are $CR^1$;
  c) E is N and A, B, and D are $CR^1$;

d) D is N and A, B, and E are CR$^1$; or e) A and D are N and B and E are CR$^1$.

22. A composition of claim 21 wherein the compound of formula (1) is one wherein A is N and B, E, and D are CR$^1$.

23. A composition of claim 22 wherein X is O.

24. A composition of claim 22 wherein X is NR$^3$.

25. A composition of claim 21 wherein the compound of formula (1) is one wherein B is N and A, E, and D are CR$^1$.

26. A composition of claim 25 wherein X is O.

27. A composition of claim 25 wherein X is NR$^3$.

28. A composition of claim 21 wherein the compound of formula (1) is one wherein E is N and A, B, and D are CR$^1$.

29. A composition of claim 28 wherein X is O.

30. A composition of claim 28 wherein X is NR$^3$.

31. A composition of claim 21 wherein the compound of formula (1) is one wherein D is N and A, B, and E are CR$^1$.

32. A composition of claim 21 wherein the compound of formula (1) is one wherein A and D are N and B and E are CR$^1$.

33. A composition of claim 32 wherein X is O.

34. A composition of claim 32 wherein X is NR$^3$.

35. A composition of claim 21 wherein the compound of formula (1) is one wherein B and D are N and A and E are CR$^1$.

36. A composition of claim 21 wherein the compound of formula (1) is one wherein E and D are N and A and B are CR$^1$.

37. A composition of claim 21 wherein the compound of formula (1) is one wherein A and E are N and B and D are CR$^1$.

38. A composition of claim 21 wherein the compound of formula (1) is one wherein A and B are N and E and D are CR$^1$.

39. A composition of claim 21 wherein the compound of formula (1) is one wherein B and E are N and A and D are CR$^1$.

40. A composition of claim 21 wherein the compound of formula (1) is one wherein A, E, and D are N and B is CR$^1$.

* * * * *